United States Patent [19]
Phan et al.

[11] Patent Number: 6,022,610
[45] Date of Patent: *Feb. 8, 2000

[54] DEPOSITION OF OSMOTIC ABSORBENT ONTO A CAPILLARY SUBSTRATE WITHOUT DELETERIOUS INTERFIBER PENETRATION AND ABSORBENT STRUCTURES PRODUCED THEREBY

[75] Inventors: Dean Van Phan, West Chester; Paul Arlen Forshey, Cincinnati, both of Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/653,876

[22] Filed: Jul. 19, 1996

Related U.S. Application Data

[63] Continuation-in-part of application No. 08/456,882, Jun. 1, 1995, abandoned, which is a continuation of application No. 08/155,040, Nov. 18, 1993, abandoned.

[51] Int. Cl.⁷ ............................................................ B32B 5/14
[52] U.S. Cl. .......................... 428/171; 428/195; 428/218; 442/417
[58] Field of Search ................................... 428/171, 195, 428/218; 442/417

[56] References Cited

U.S. PATENT DOCUMENTS

| | | | |
|---|---|---|---|
| Re. 32,649 | 4/1988 | Brandt et al. | 604/368 |
| 3,369,700 | 2/1968 | Nelson | 221/63 |
| 3,554,788 | 1/1971 | Fechillas | 117/140 |
| 3,670,731 | 6/1972 | Harmon | 128/284 |
| 3,721,242 | 3/1973 | Krusko | 128/287 |
| 3,849,173 | 11/1974 | Drelich et al. | 117/62.1 |
| 3,881,632 | 5/1975 | Early et al. | 221/50 |
| 3,965,904 | 6/1976 | Mesek et al. | 128/284 |
| 3,993,820 | 11/1976 | Repke | 428/167 |
| 4,008,353 | 2/1977 | Gross et al. | 428/522 |
| 4,061,846 | 12/1977 | Gross et al. | 526/16 |
| 4,071,650 | 1/1978 | Gross | 428/260 |
| 4,082,878 | 4/1978 | Boe et al. | 428/195 |

(List continued on next page.)

FOREIGN PATENT DOCUMENTS

| | | |
|---|---|---|
| 0033988 A2 | 8/1981 | European Pat. Off. . |
| 0040087 A2 | 11/1981 | European Pat. Off. . |
| 0 160 572 | 11/1985 | European Pat. Off. . |
| 0257308 A2 | 3/1988 | European Pat. Off. . |
| 0262405 A2 | 4/1988 | European Pat. Off. . |
| 0 291 316 A2 | 11/1988 | European Pat. Off. . |
| 0290814 A2 | 11/1988 | European Pat. Off. . |
| 0293762 A2 | 12/1988 | European Pat. Off. . |
| 0304952 A2 | 3/1989 | European Pat. Off. . |
| 63-291908 | 11/1988 | Japan . |
| 1452325 | 10/1976 | United Kingdom . |

OTHER PUBLICATIONS

Patent Application Serial No. 08/154,667, Filed Nov. 17, 1993 in the names of Trokhan et al., entitled "Process of Making Absorbent Structures and Absorbent Structures Produced Thereby."

Patent Application Serial No. 08/155,040, Filed Nov. 18, 1993 in the names of Phan et al., entitled "Deposition of Osmotic Absorbent onto a Capillary Substrate without Deleterious Interfiber Penetration and Absorbent Structures Produced Thereby."

*Primary Examiner*—Jenna Davis
*Attorney, Agent, or Firm*—Theodore P. Cummings; Jeffrey V. Bamber; Steven W. Miller

[57] ABSTRACT

An absorbent structure comprising freestanding osmotic absorbent sites disposed on or within a capillary substrate. The sites extend outwardly normal to the plane of the absorbent structure or fill apertures within the plane of the absorbent structure. Upon imbibing liquids, the sites of osmotic absorbent can expand without constraint from the substrate.

8 Claims, 2 Drawing Sheets

U.S. PATENT DOCUMENTS

| | | | |
|---|---|---|---|
| 4,145,464 | 3/1979 | McConnell et al. | 428/171 |
| 4,235,237 | 11/1980 | Mesek et al. | 128/284 |
| 4,293,600 | 10/1981 | Fink et al. | 427/385.5 |
| 4,310,593 | 1/1982 | Gross | 428/290 |
| 4,354,487 | 10/1982 | Oczkowski et al. | 128/156 |
| 4,460,642 | 7/1984 | Errede et al. | 428/283 |
| 4,529,480 | 7/1985 | Trokhan | 162/109 |
| 4,559,050 | 12/1985 | Iskra | 604/368 |
| 4,699,823 | 10/1987 | Kellenberger et al. | 428/219 |
| 4,715,918 | 12/1987 | Lang | 156/273.1 |
| 4,735,738 | 4/1988 | Willman | 252/90 |
| 4,748,076 | 5/1988 | Saotome | 428/224 |
| 4,761,322 | 8/1988 | Raley | 428/198 |
| 4,820,294 | 4/1989 | Morris | 604/383 |
| 4,835,020 | 5/1989 | Itoh et al. | 427/389.9 |
| 4,842,927 | 6/1989 | Itoh et al. | 428/254 |
| 4,865,886 | 9/1989 | Itoh et al. | 427/342 |
| 4,880,419 | 11/1989 | Ness | 604/368 |
| 4,888,238 | 12/1989 | Katz et al. | 428/378 |
| 4,892,754 | 1/1990 | Itoh et al. | 427/54.1 |
| 4,994,053 | 2/1991 | Lang | 604/367 |
| 5,013,309 | 5/1991 | Baigas, Jr. et al. | 604/368 |
| 5,071,681 | 12/1991 | Manning et al. | 427/392 |
| 5,079,034 | 1/1992 | Miyake et al. | 427/45.1 |
| 5,118,376 | 6/1992 | Pigneul et al. | 156/219 |
| 5,149,335 | 9/1992 | Kellenberger et al. | 604/372 |
| 5,156,902 | 10/1992 | Pieper et al. | 428/206 |
| 5,171,391 | 12/1992 | Chmielewski et al. | 156/229 |
| 5,175,046 | 12/1992 | Nguyen | 428/198 |
| 5,242,435 | 9/1993 | Murji et al. | 604/374 |
| 5,281,207 | 1/1994 | Chmielewski et al. | 604/378 |
| 5,487,736 | 1/1996 | Van Phan | 604/368 |

DEPOSITION OF OSMOTIC ABSORBENT ONTO A CAPILLARY SUBSTRATE WITHOUT DELETERIOUS INTERFIBER PENETRATION AND ABSORBENT STRUCTURES PRODUCED THEREBY

This is a continuation-in-part of application Ser. No. 08/456,882, filed on Jun. 1, 1995, now abandoned, which is a continuation application of Ser. No. 08/155,040, filed Nov. 18, 1993, now abandoned.

FIELD OF THE INVENTION

This invention relates to capillary substrates having osmotic absorbent capabilities, more particularly to capillary substrates having an osmotic absorbent which may freely expand upon imbibing liquids.

BACKGROUND OF THE INVENTION

Absorbent structures comprising a capillary absorbent substrate and having an osmotic absorbent applied thereto are known in the art. As used herein, a "capillary" absorbent structure absorbs liquids, such as water, by capillary attraction of the liquids due to the thermodynamic force of attraction between a liquid and the solid surface of the capillary medium. In contrast, as used herein, an "osmotic" absorbent structure absorbs liquids deposited thereon by equalization of differential partial fluid pressure in the absence of ion exchange, forming a gelatinous substance which imbibes the liquids. As used herein, an "absorbent structure" refers to materials which, in combination, absorb liquids by both osmotic and capillary absorptions.

The capillary absorbent may be provided in the form of a substrate, for the osmotic absorbent to be later applied thereupon. Typically the capillary absorbent substrate is a generally planar, almost two-dimensional material, such as paper, nonwoven fabric, woven fabric, or even formed film, having two principal directions and a thickness in the third direction.

As used herein, the X-Y plane refers to the plane of the absorbent structure 20 as it is laid flat on a horizontal surface. The Z-direction is the direction extending outwardly from and orthogonal to the X-Y plane.

The osmotic absorbent may be made of acrylic acid, starch grafted acrylate copolymers, etc. Such osmotic absorbent materials are commonly used as absorbent gelling materials or superabsorbers in disposable absorbent articles such as diapers and sanitary napkins. The osmotic absorbent may be applied to the substrate in the form of a liquid precursor, to be later cured into an osmotic absorbent.

The osmotic absorbent material may be applied to the capillary absorbent substrate as a liquid precursor, such as a liquid monomer, then crosslinked to form an absorbent polymeric material. Usually the liquid precursor is applied to the capillary absorbent substrate in a liquid form and typically comprises some form of acrylic acid.

Typically, the liquid precursor is applied to the absorbent substrate by spraying, impregnation, etc. to provide a uniform coating thereon. Other teachings in the art suggest discontinuous applications of the liquid precursor to the substrate through brushing, roller coating, etc. Once the liquid precursor is applied to the capillary absorbent substrate, the liquid precursor may be crosslinked through elevated temperature, irradiation, etc.

Examples of such attempts in the art include U.S. Pat. No. 4,008,353 issued Feb. 15, 1977 to Gross et al., U.S. Pat. No. 4,061,846 issued Dec. 6, 1977 to Gross et al.; U.S. Pat. No. 4,071,650 issued Jan. 31, 1978 to Gross; U.S. Pat. No. 4,835,020 issued May 30, 1989 to Itoh et al.; U.S. Pat. No. 4,842,927 issued Jun. 27, 1989 to Itoh et al.; U.S. Pat. No. 4,865,886 issued Sep. 12, 1989 to Itoh et al., U.S. Pat. No. 4,892,754 issued Jan. 9, 1990 to Itoh et al.; U.S. Pat. No. 5,079,032 issued Nov. 21, 1988 to Miyake et al. and Great Britain Patent 1,452,325 published October, 1976 in the name of Triopolis.

However, deposition of an osmotic absorbent onto a capillary substrate according to the prior art can present serious problems. For example, typically the osmotic absorbent is introduced to the substrate as a liquid precursor, as noted above. The liquid precursor, of course, flows by capillary attraction throughout the entirety of or throughout particular regions of the capillary substrate onto which the liquid precursor was deposited, until the liquid precursor is absorbed. The liquid precursor is then cured into an osmotic absorbent which is dispersed throughout the capillary substrate in a three-dimensional matrix.

When a liquid insults the absorbent structure, the osmotic absorbent begins to swell upon imbibing the liquids. However, the osmotic absorbent is constrained from swelling by the three-dimensional fibrous matrix of the capillary substrate. If osmotic absorbent is unable to swell—due to the constraints of the fibers in the capillary substrate—the osmotic absorbent will not reach its full absorptive capacity. The liquids intended to be absorbed by the absorbent substrate may breach the perimeter of the absorbent substrate, resulting in leakage.

Further liquid insults will not be absorbed by the absorbent structure, because the osmotic absorbent cannot be utilized to its full capacity. Instead, additional liquid insults will run off the absorbent structure and breach its perimeter.

Absorbent liquids running off or breaching the perimeter of the absorbent structure can be particularly disastrous if the absorbent structure is used in the core of a disposable absorbent article, such as a diaper or a sanitary napkin. Osmotic absorbents, capillary absorbents, and combinations thereof have long been used in disposable absorbent articles. However, with the advances in this art, the consumer has come to expect disposable absorbent articles which rapidly absorb liquid insults and do not leak under normal wearing conditions.

Accordingly, it is an object of this invention to provide an absorbent structure having osmotic and capillary absorbing capabilities. It is further an object of this invention to provide such a structure wherein the osmotic absorbent is not constrained from swelling by a capillary substrate upon imbibing liquids. It is further an object of this invention to provide an absorbent structure having these characteristics and which provides new benefits not previously known in the art for use in disposable absorbent articles, particularly maintaining the pattern of an osmotic absorbent on a capillary substrate during the life of the disposable absorbent article.

BRIEF SUMMARY OF THE INVENTION

The invention comprises an absorbent structure. The absorbent structure has a generally planar capillary substrate and at least one site of osmotic absorbent. The osmotic absorbent is joined to the capillary substrate at a proximal end and extends to a distal end freestanding from the capillary substrate. The distal end of the osmotic absorbent can expand upon imbibing liquids.

The capillary substrate defines an X-Y plane and a Z-direction orthogonal to the X-Y plane. In one embodiment, the osmotic absorbent extends outwardly from the capillary substrate in the Z-direction and can expand in the X-Y plane without constraint from the capillary substrate upon imbibing liquids. In a second embodiment, the capillary substrate may be apertured. The osmotic absorbent is distributed in the apertures and can expand in the Z-direction without constraint from the capillary substrate upon imbibing liquids.

BRIEF DESCRIPTION OF THE DRAWINGS

While the Specification concludes with claims particularly pointing out and distinctly claiming the present invention, it is believed the same will be better understood from the following description taken in conjunction with the accompanying drawings in which:

DETAILED DESCRIPTION OF THE INVENTION

Figure 1:
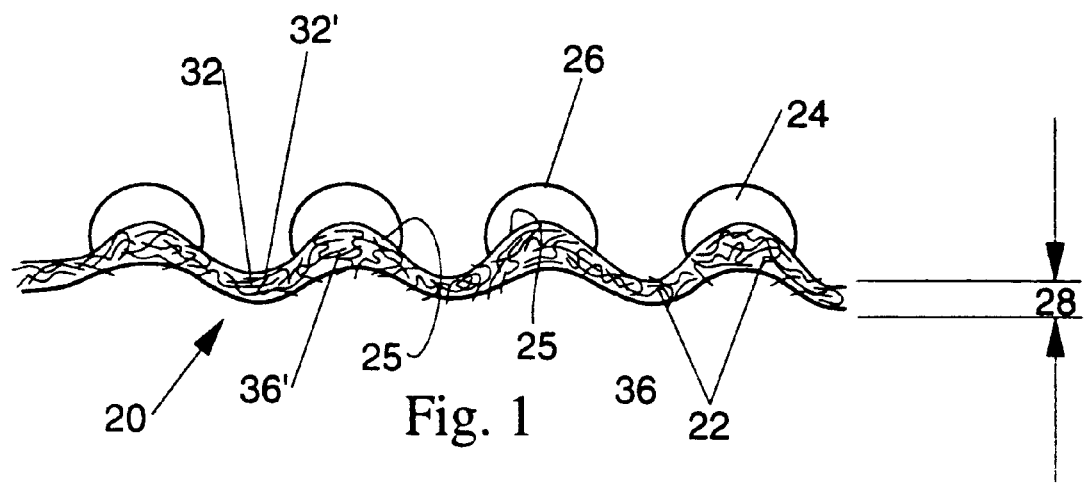
FIG. 1 is an elevational view of an absorbent structure according to the present invention having the osmotic absorbent freestanding in the Z-direction.

Referring to FIG. 1, the absorbent structure 20 according to the present invention comprises a capillary substrate 22 and an immobilized non-particulate osmotic absorbent 24 joined to the capillary substrate 22 at a proximal end 25 and freestanding therefrom. By "freestanding" it is meant that the osmotic absorbent 24 extends outwardly from the capillary substrate 22 such that a particular distal end 26 of the osmotic absorbent 24 is remotely disposed from at least one edge of or at least one face of the capillary substrate 22. It is to be recognized, of course, that a freestanding distal end 26 of the osmotic absorbent 24 may be contained within the perimeter of the capillary substrate 22 of the absorbent structure 20, and still be freestanding. By "immobilized" it is meant that the proximal end 25 of the osmotic absorbent 24 cannot move relative to the capillary substrate 22 without destruction or unintended gross deformation of at least one of the proximal ends 25 of the osmotic absorbent 24 and/or capillary substrate 22 occurring By "non-particulate" it is meant that the osmotic absorbent 24, as immobilized on the capillary substrate 22, assumes whatever form or shape is necessary to conform to the capillary substrate 22 under the influences of gravity, viscosity, etc. Non-particulate osmotic absorbent 24 is not applied to the capillary substrate in a predefined shape such as occurs with, for example, particulates, chunks, granular pieces, or other discrete pieces of osmotic absorbent.

Figure 2:
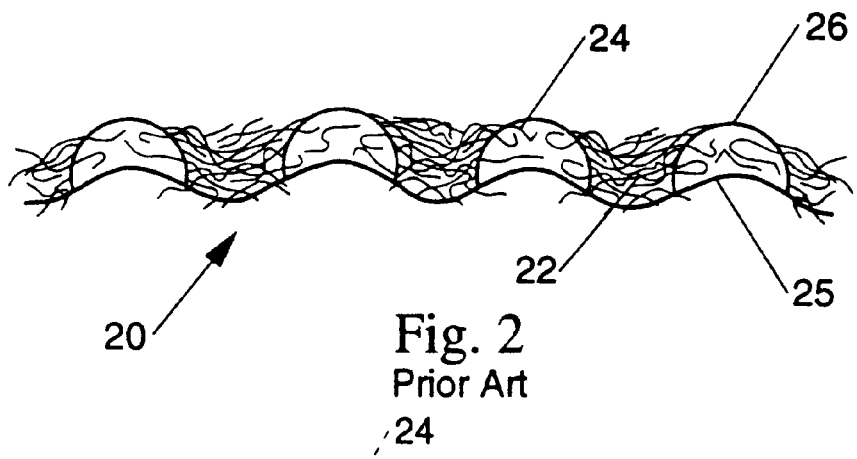
FIG. 2 is an elevational view of an absorbent structure according to the prior art.

In contrast, as illustrated in FIG. 2, absorbent structures 20 according to the prior art teach an osmotic absorbent 24 which penetrate throughout the thickness of the capillary substrate 22. This arrangement provides the disadvantage that, as discussed above, the osmotic absorbent 24 is constrained by the capillary substrate 22 and cannot expand upon imbibing liquids. Such constraint from expansion prevents the osmotic absorbent 24 from absorbing all of the liquid insults, and limits the capacity of the absorbent structure 20 according to the prior art.

The osmotic absorbent 24 may be applied to the capillary substrate 22 as an osmotic precursor, typically in the form of a liquid precursor. The liquid precursor may be applied to the capillary substrate 22 in a particular pattern. Once the liquid precursor is disposed on the capillary substrate 22, the liquid precursor is immobilized and may be polymerized in situ to form the osmotic absorbent 24.

The capillary substrate 22 is generally planar, and preferably, though not necessarily, cellulosic. The capillary substrate 22 may comprise multiple regions having different basis weights (including zero basis weight apertures), different topographical elevations 28, and/or different densities. Alternatively, the capillary substrate 22 may comprise a single region.

If the capillary substrate 22 comprises multiple regions of different densities, any arrangement is acceptable, providing the capillary substrate 22 is generally planar, the osmotic absorbent 24 may be immobilized thereon in a freestanding pattern, and the capillary substrate 22 absorbs and transports liquids deposited thereon by capillary mechanisms.

Figure 3:
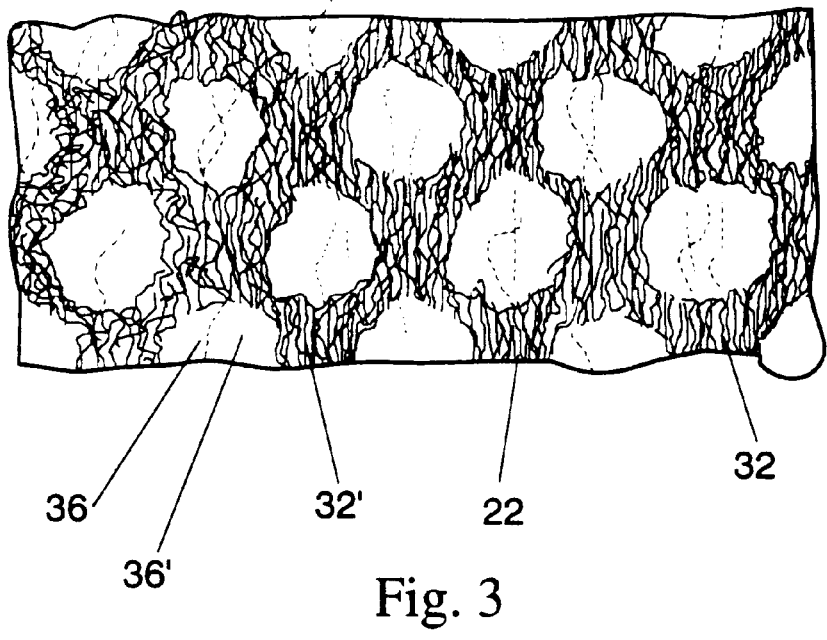
FIG. 3 is a top plan view of the absorbent structure of FIG. 1, showing the fibers of the capillary substrate in phantom.

Referring to FIG. 3, the capillary substrate 22 may have distinguishable regions defining two mutually different densities. Preferably such regions are disposed in an arrangement comprising a high density essentially continuous network region 32 and discrete low density regions 36 within the essentially continuous network. As used herein, a region which extends substantially throughout the capillary substrate 22 in one or both principal directions is considered to be "an essentially continuous network." Conversely, regions which are not contiguous, are considered to be "discrete." Preferably the discrete regions 36 and essentially continuous network region 32 are disposed in a nonrandom repeating pattern. By being "nonrandom" the regions are considered to be predictable and may occur as the result of known and predetermined features of the manufacturing process. By "repeating" the pattern is formed more than once in the capillary substrate 22. However, it is to be understood that if the capillary substrate 22, as presented to the consumer, is relatively small and the pattern is relatively large or the absorbent structure 20 is presented to the consumer as an integral unit, the pattern may appear to occur only once in the capillary substrate 22. For example, if the absorbent structure 20 is utilized in a disposable absorbent article, such as a diaper or sanitary napkin, the pattern may occur only once in such disposable absorbent article, but repeats during the manufacture of multiple disposable absorbent articles.

For the embodiments described herein, a capillary substrate 22 having a plurality, of such as about 2 to about 155, low density discrete regions 36 (preferably with a freestanding site of osmotic absorbent 24 thereon) per square centimeter (10 to 1000 discrete regions 36 per square inch) and more particularly, about 4 to about 39 low density discrete regions 36 per square centimeter (25 to 250 discrete regions 36 per square inch) has been found suitable. Of course, the absorbent structure 20 according to the present invention may have only one site of osmotic absorbent 24 thereon. However, it is preferred that at least one site, and preferably a plurality of sites of osmotic absorbent 24 be provided on the capillary substrate 22, as discussed above.

The capillary substrate 22 according to the present invention may comprise two different elevations 28. The "elevation" of a capillary substrate 22 is its local deviation from planarity. The elevation 28 of a capillary substrate 22 is determined by laying it on a flat, horizontal surface, which serves as a reference plane. Different elevations 28 of the capillary substrate 22, which may or may not be coincident with the regions of differing density described above, are determined by the difference in height above the reference plane, taken orthogonal the reference plane and the principal dimensions of the capillary substrate 22.

Preferably the regions defined according to differing densities and differing elevations 28 are coincident as illustrated by FIG. 1. Thus the discrete low density regions 36' are also raised in elevation 28 (or lowered in elevation 28 if the capillary substrate 22 is inverted) from the high density region 32'. However, it is to be recognized that suitable embodiments may exist wherein such discrete regions 36 of a particular density are not coincident with a particular elevation 28.

A particularly preferred capillary substrate 22 is through-air dried and produced in accordance with commonly assigned U.S. Pat. No. 4,529,480 issued Jul. 16, 1985 to Trokhan, which patent is incorporated herein by reference for the purpose of showing a through-air-dried capillary substrate 22 having discrete regions 36 and an essentially continuous pattern and for the purpose of showing how to make a particularly preferred capillary substrate 22 according to the present invention having different elevations 28. A capillary substrate 22 made according to commonly assigned U.S. Pat. No. 4,529,480 issued Jul. 16, 1985 to Trokhan has mutually coincident discrete regions 36, which regions are both relatively low in density and raised (or lowered) in elevation 28.

The capillary substrate 22 according to the present invention may be comprised of cellulosic fibers having one very large dimension (along the longitudinal axis of the fiber) compared to the other two relatively very small dimensions (mutually perpendicular, and being both radial and perpendicular to the longitudinal axis of the fiber), so that linearity is approximated. While microscopic examination of the fibers may reveal the other two dimensions are small compared to the principal dimension of the fibers, such other two small dimensions need not be substantially equivalent nor constant throughout the axial length of the fiber. It is only important that the fiber be able to bend about its axis, be able to bond to other fibers and be distributed onto a forming wire (or its equivalent) by a liquid carrier.

The capillary substrate 22 may be creped or be uncreped, as desired. Creping the capillary substrate 22 foreshortens it producing undulations in the Z-direction. Such undulations yield cross machine ripples which are considered too minor to be differences in elevation 28 as compared to the differences in elevation 28 obtainable by the methods described hereinbelow. However, it is to be recognized that a creped capillary substrate 22 may be embossed, through-air-dried, etc. to produce differences in elevation 28 which are large, relative to the creping undulations and ripples.

The fibers comprising the capillary substrate 22 may be synthetic, such as polyolefin or polyester; are preferably cellulosic, such as cotton linters, rayon or bagasse; and more preferably are wood pulp, such as soft woods (gymnosperms or coniferous) or hard woods (angiosperms or deciduous), may be cross-linked, and may comprise combinations of synthetic and cellulosic materials. As used herein, a capillary substrate 22 is considered "cellulosic" if the capillary substrate 22 comprises at least about 50 weight percent or at least about 50 volume percent cellulosic fibers, including but not limited to those fibers listed above. A cellulosic mixture of wood pulp fibers comprising softwood fibers having a length of about 2.0 to about 4.5 millimeters and a diameter of about 25 to about 50 micrometers, and hardwood fibers having a length of less than about 1 millimeter and a diameter of about 12 to about 25 micrometers has been found to work well for the capillary substrates 22 described herein.

If wood pulp fibers are selected for the capillary substrate 22, the fibers may be produced by any pulping process including chemical processes, such as sulfite, sulfate and soda processes; and mechanical processes such as stone groundwood. Alternatively, the fibers may be produced by combinations of chemical and mechanical processes or may be recycled. The type, combination, and processing of the fibers used are not critical to the present invention.

A capillary substrate 22 according to the present invention is macroscopically two-dimensional and generally planar, having some thickness in the third dimension (coincident the Z-direction). However, the thickness in the third dimension is relatively small compared to the first two dimensions or to the capability to manufacture a capillary substrate 22 having relatively large measurements in the first two dimensions.

The capillary substrate 22 according to the present invention comprises a single lamina. However, it is to be recognized that two or more single laminae, any or all made according to the present invention, may be joined in face-to-face relation to form a unitary laminate. A capillary substrate 22 according to the present invention is considered to be a "single lamina" if it is taken off the forming wire, or its equivalent, as a single sheet having lo a thickness prior to drying which does not change unless fibers are added to or removed from the sheet. The capillary substrate 22 may be later embossed, or remain nonembossed, as desired.

Of course, it is to be recognized that a woven or nonwoven material may be adequately utilized as a capillary substrate 22, or furthermore, that a formed film may be utilized, providing it meets the capillarity/density/elevational requirements specified above.

A capillary substrate 22 having different densities may be achieved by locally densifying certain areas, such as the discrete regions 36, through embossing as is well known in the art, or by dedensifying certain areas by through-air drying as is well known in the art. Similarly, a capillary substrate 22 having different elevations 28 in the direction generally normal to the plane of the capillary substrate 22 may be accomplished by nested embossing as is well known in the art, or again may be accomplished by through air drying as is well known in the art.

A particularly preferred capillary substrate 22 is produced in accordance with the aforementioned U.S. Pat. No. 4,529,480 issued to Trokhan, which patent is incorporated herein by reference for the purpose of showing a capillary substrate 22 having discrete regions 36 and an essentially continuous pattern and for the purpose of showing how to make a particularly preferred capillary substrate 22 according to the present invention having different elevations 28. A capillary substrate 22 made according to U.S. Pat. No. 4,529,480 issued to Trokhan has mutually coincident discrete regions 36 which are both relatively low in density and raised (or lowered) in elevation 28 relative to the essentially continuous network region 32.

The osmotic absorbent 24 may comprise any osmotic precursor, typically a liquid precursor, which can be applied to the capillary substrate 22. As used herein a "precursor" refers to any material which transforms to an osmotic absorbent 24 upon curing or polymerizing. As used herein an "osmotic absorbent" refers to any material which has the capability to absorb at least 10 times its own weight of any aqueous solution, and preferably synthetic urine, on a grams per gram basis.

The synthetic urine comprises a salt solution in distilled water with a surface tension adjusted to 45 dynes per centimeter with about 0.0025% octylphenoxy polyethoxy ethanol surfactant (Triton X-100, from Rohm and Haas Company). The synthetic urine solution comprises 15 parts of 1% Triton X-100, 60 parts NaCl, 1.8 parts of $CaCl_2.2H_2O$, 3.6 parts of $MgCl_2.6H_2O$ and 6000 parts of distilled water.

Preferred osmotic absorbents 24 include copolymers of sodium acrylate and acrylic acid, starch grafted acrylate copolymers, cross-linked carboxymethyl cellulose, etc. Any liquid precursor which can be cured into a solid osmotic absorbent 24 is suitable. A particularly preferred liquid precursor, and ultimately osmotic absorbent 24 for use in the present invention, comprises polymers of sodium acrylate, and acrylic acid, carboxymethyl cellulose, a photo-initiator and a cross-linker.

A preferred liquid precursor is a substantially water-soluble monomer comprising neutralized or neutralizable carboxyl groups. The monomer preferably contains sufficient carboxyl groups such that a linear polymer thereof is substantially water-soluble (i.e., the carboxyl groups are hydrophilic). Mixtures of such monomers may also be used.

The monomers comprising carboxyl groups include acid, acid anhydride, and ester group containing monomers. These monomers may also contain other hydrophilic groups, such as hydroxyl groups, amide-groups, amino groups, nitrile groups, and quaternary ammonium salt groups. Preferably, the monomer contains acid type hydrophilic groups. More preferably, the monomer contains at least about 5 mole percent, most preferably at least about 10 mole percent, of acid groups.

Monomers containing carboxyl groups include the olefinically unsaturated acids, esters thereof, and anhydrides which contain at least one carbon to carbon olefinic double bond. More specifically, these monomers can be selected from olefinically unsaturated carboxylic acids, esters of such carboxylic acids, acid anhydrides, sulfonic acids, esters of such sulfonic acids, and mixtures of any two or more of the foregoing monomers.

Olefinically unsaturated carboxylic acid and carboxylic acid anhydride monomers include the acrylic acids and derivatives thereof, typified by acrylic acid itself, methacrylic acid, ethacrylic acid, alpha-chloroacrylic acid, alpha-cyano acrylic acid, beta-methyl acrylic acid (i.e., crotonic acid), alpha-phenyl acrylic acid, beta-acryloxy propionic acid, and beta-steryl acrylic acid; maleic acid; and maleic acid anhydride. Other monomers of this type are sorbic acid, alpha-chloro sorbic acid, angelic acid, cinnamic acid, p-chloro cinnamic acid, itaconic acid, citraconic acid, mesaconic acid, glutaconic acid, aconitic acid, fumaric acid, and tricarboxyethylene.

Olefinically unsaturated sulfonic acid monomers and derivatives thereof include aliphatic or aromatic vinyl sulfonic acids such as vinylsulfonic acid, allyl sulfonic acid, vinyltoluene sulfonic acid and styrene sulfonic acid; and acrylic and methacrylic sulfonic acid derivatives such as sulfoethyl acrylate, sulfoethyl methacrylate, sulfopropyl acrylate, sulfopropyl methacrylate, 2-hydroxy-3-acryloxy propyl sulfonic acid, 2-hydroxy-3-methacryloxy propyl sulfonic acid and 2-acrylamido-2-methyl propane sulfonic acid.

The carboxyl groups (e.g., acid groups) are at least partially neutralized with cations capable of forming a salt with the monomer to form a monomer having neutralized carboxyl groups. Such salt-forming cations include, for example, alkali or alkaline metals, ammonium, substituted ammonium and amines as discussed in further detail in U.S. Pat. No. Re. 32,649, Brandt et al., Apr. 19, 1988, incorporated herein by reference for the purpose of showing suitable osmotic absorbents 24. Neutralization is preferably carried out in any conventional manner which results in at least about 25 mole percent, more preferably at least about 50 mole percent, most preferably at least about 75 mole percent, of the total carboxyl groups being neutralized. The carboxyl groups are preferably neutralized prior to formation of the substantially water-insoluble polymer, e.g., neutralization is preferably carried out on the monomer or a water-soluble polymer thereof Monomers possessing hydrophilic groups other than carboxyl groups may be used with the carboxyl group containing monomer. Other hydrophilic groups include hydroxyl groups, amide-groups, amino groups, nitrile groups, and quaternary ammonium salt groups. Monomers containing such groups are well known materials and are described in greater detail, for example, in U.S. Pat. No. 4,076,663 issued to Masuda et al. on Feb. 28, 1978; and U.S. Pat. No. 4,062,817 issued to Westerman on Dec. 13, 1977; which patents are incorporated herein by reference. One or more types of such hydrophilic groups may be present in the monomer.

Although this disclosure is generally in terms of the liquid precursor, it is to be understood that substantially water-soluble homopolymers, copolymers, or reaction products of the monomer may also be used in place of or in addition to the monomer form. Such alternative starting materials include substantially water-soluble homopolymers of the monomer and substantially water-soluble reaction products of the monomer or its homopolymer and the internal crosslinking agent. For example, a substantially linear, substantially water-soluble osmotic absorbent 24 can be formed by subjecting the liquid precursor to known polymerization conditions. A substantially water-soluble, partially crosslinked osmotic absorbent 24 may also be formed by reacting (e.g., by heating) the liquid precursor or linear polymer thereof with a crosslinking agent such as the internal crosslinking agents herein. Such a osmotic absorbent 24 would typically have a low level of crosslinking, e.g., less than about 5%.

The specific type of liquid precursor selected is not critical to the invention, so long as the liquid precursor may be applied in the desired pattern, and immobilized, so that the liquid precursor remains freestanding and does not flow, migrate, or is otherwise transported to different parts of the capillary substrate 22 and transmogrify the resulting freestanding osmotic absorbent 24 into a less useful disposition, such as one penetrating through the thickness of the capillary substrate 22. Such transmogrification may result in an absorbent structure 20 in which the capillary substrate 22 constrains the osmotic absorbent 24 from expanding upon imbibing liquids, and limits the capacity of the absorbent substrate.

The osmotic absorbent 24 may be applied to the capillary substrate 22 in liquid form, such as the liquid precursor discussed above. Preferably when applied to the capillary substrate 22 the liquid precursor has a kinematic viscosity of at least about 2,000 centipoises, as measured by a Brookfield viscometer using a number 2 Shell cup at 20° C., and preferably a kinematic viscosity of at least about 4,000 centipoises. Such a viscosity is necessary to keep a distal portion of the liquid precursor freestanding until it is cured into a solid osmotic absorbent 24 polymer by crosslinking. Preferably the viscosity does not exceed 10,000 centipoises.

A kinematic viscosity of at least about 2,000 centipoises may be achieved by adding a thickening agent to the liquid precursor prior to its application to the capillary substrate 22. Suitable thickening agents include polyvinyl pyrolodine, hydroxyethyl cellulose, preferable carboxymethylcellulose and polyacrylic acid. The thickening agent may be added in a concentration of 2 percent by weight thickening agent per liter of liquid precursor.

If one does not wish to add a thickening agent to the liquid precursor, an acrylic acid type liquid precursor can be partially prepolymerized. Prepolymerization not only increases the viscosity, but also allows for removal of residual monomers before the liquid precursor is applied to the capillary substrate 22. Minimizing residual monomers in the resulting osmotic absorbent 24 is highly desirable if the absorbent structure 20 is to be utilized in a disposable absorbent article, such as a diaper or sanitary napkin, or is to be utilized in other applications where epidermal contact may occur.

Figure 4:
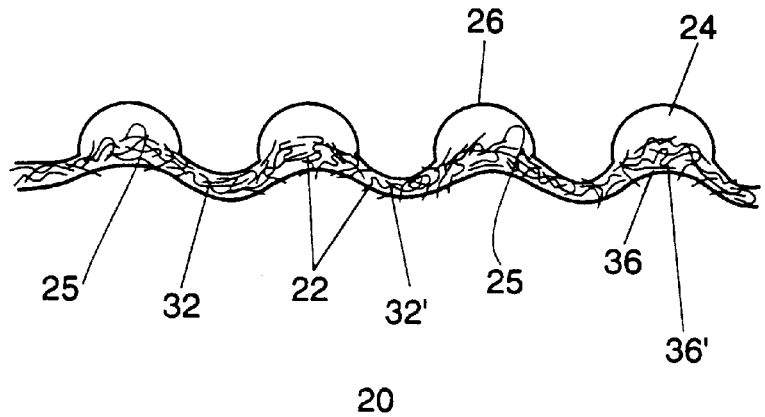
FIG. 4 is an elevational view of an alternative embodiment according to the present invention having interfiber penetration at the proximal end of the freestanding osmotic absorbent.

Referring to FIG. 4, if desired, the rheology of the liquid precursor may be tailored to the density and void volume of the capillary substrate 22 so that the liquid precursor penetrates into the capillary substrate 22 in the Z-direction. This arrangement results in interfiber penetration of the proximal end 25 of the freestanding osmotic absorbent 24. Of course, a residual portion, comprising the distal end 26 of the liquid precursor, must remain freestanding, as described above with reference to FIGS. 2 and 3. However, the arrangement of FIG. 4 provides the advantage there will be generally greater adhesion of the osmotic absorbent 24 to the capillary substrate 22, due to the entanglement and penetration of the fibers of the capillary substrate 22 with the cured osmotic absorbent 24.

To provide interfiber penetration of the proximal end 25 of the freestanding osmotic absorbent 24, generally the liquid precursor which is later cured to an osmotic absorbent 24 should have a somewhat lesser viscosity. However, the viscosity should not be so low that the liquid precursor wicks throughout the capillary substrate 22, and a distal end 26 of the osmotic absorbent 24 does not remain freestanding, as occurs in the prior art. Alternatively, a capillary substrate 22 of a lesser density and higher void volume may be selected, providing the capillary substrate 22 does not allow the liquid precursor to completely wick throughout and thereby not have a freestanding distal end 26.

The freestanding osmotic absorbent 24 is in situ polymerized, to prevent it from wicking throughout the capillary substrate 22. In situ polymerization may be accomplished by irradiating the osmotic absorbent 24 under radiation having a wave length sufficient to crosslink and cure the osmotic absorbent 24. Typically, UV light has been found to work well.

Increasing the viscosity of the liquid precursor 40 to at least 2,000 centipoises prior to deposition on the capillary substrate 22 also retards separation of the various components of the liquid precursor 40. By retarding such separation, or chromatographing of the components of the liquid precursor 40, the desired reaction mixture is maintained during polymerization. For example, in aqueous liquid precursors 40 the proper amount of water is maintained to prevent component polymerizable material from becoming insolubilized. Insolubilized polymerizable material negatively affects the polymerization reaction, and hence the ultimate performance of the osmotic absorbent 24.

Figure 5:
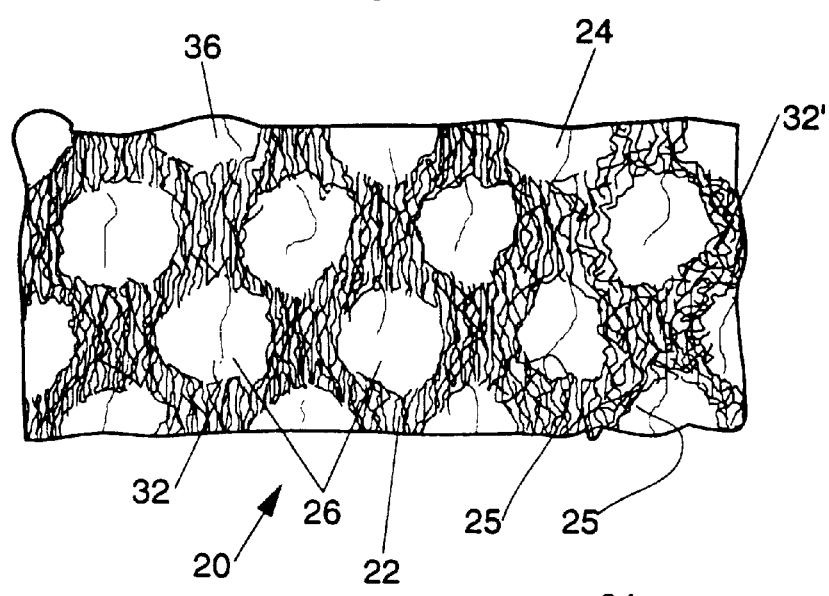
FIG. 5 is a top plan view of another alternative embodiment of an absorbent structure according to the present invention having an apertured capillary substrate and the osmotic absorbent freestanding in the X-Y plane.

Referring to FIG. 5, if desired, the capillary substrate 22 may be apertured. As used herein a "apertured" capillary substrate 22 refers to a capillary substrate 22 having one or more holes extending fully or partially therethrough, representing discrete regions 36 in an essentially continuous network region 32. Such a capillary substrate 22 may be easily manufactured, as is well known in the art, by providing a forming wire having a plurality of protuberances raised above the elevation of the furnish deposited on the forming wire during the manufacturing process. The geometry in spacing of the apertures will conform to that of the protuberances which are above the elevation of the furnish during manufacture. Alternatively, the apertures may be embossed into, cut or punched out of the capillary substrate 22 as is well known in the art.

As used herein "apertures" are inclusive of through holes, as discussed above, and blind holes. Blind hole apertures may be compressed into the capillary substrate 22 by embossing. Of course, if the discrete regions 36 are embossed into the capillary substrate 22, the discrete regions 36 will have a density greater than the essentially continuous network region 32. Either density gradient is suitable, providing the osmotic absorbent 24 within the aperture is free to expand without constraint from the capillary substrate 22 upon imbibing liquids. A capillary substrate 22 having apertures as through holes is generally preferred over a capillary substrate 22 having apertures as blind holes, because the osmotic absorbent 24 within the through holes is free to expand outwardly from the X-Y plane in both senses (i.e., in opposed directions) of the Z-direction. Further, such a capillary substrate 22 need not be oriented towards the direction of the liquid insults.

Figure 6:
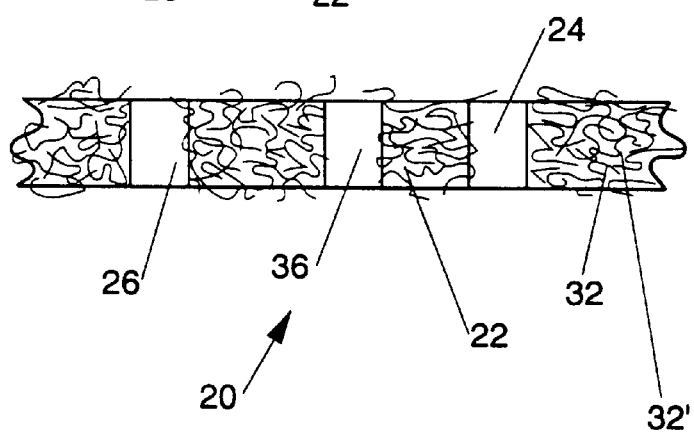
FIG. 6 is an elevational view of the absorbent structure of FIG. 5, taken along line 6—6 of FIG. 5 showing the through holes of the apertures.

The liquid precursor may be deposited in the apertures, filling the space of these discrete regions 36 within the essentially continuous network region 32. This arrangement provides an absorbent structure 20 having freestanding sites of an osmotic absorbent 24 with the ability to swell in opposed senses in the Z-direction, but which is limited from swelling in the X-Y plane as illustrated in FIG. 6. If desired, the proximal ends 25 of the osmotic absorbent 24 sites may display interfiber penetration, as discussed above.

It will be apparent that the embodiment of FIGS. 1 and 3–4 have sites of osmotic absorbent 24 which are freestanding in the Z-direction. The embodiment of FIGS. 5–6 have sites of osmotic absorbent 24 which are freestanding within the X-Y plane. Of course, combinations of these embodiments are feasible, wherein the osmotic absorbent 24 is freestanding in both the X-Y plane and the Z-direction.

The difference between the embodiments of FIGS. 1 and 3–4 having osmotic absorbent 24 freestanding in the Z-direction and the embodiments of FIGS. 5–6 having osmotic absorbent 24 freestanding in the X-Y plane is that in the embodiment of FIGS. 1 and 3–4 the osmotic absorbent 24 can expand in the X-Y plane without constraint by the capillary substrate 22 upon imbibing liquids. The osmotic absorbent 24 in the embodiment of FIGS. 5–6 can expand in the Z-direction without constraint by the capillary substrate 22 upon imbibing liquids. Of course, the osmotic absorbent 24 in the embodiment of FIGS. 1 and 3–4 will incur some expansion in the Z-direction, particularly the embodiment of FIG. 4 having interfiber penetration at the proximal end 25 of the site of the osmotic absorbent 24. While the foregoing does not suggest no expansion against the constraint of the fibers of the capillary substrate 22 will occur according to the present invention, the unconstrained expansion will be in the plane or directions generally opposite such constraints.

In another variation (not shown), an essentially continuous pattern can be embossed into the capillary substrate 22 using rolls having a corresponding pattern, as is well known in the art. By embossing an essentially continuous pattern into the capillary substrate 22, the osmotic absorbent 24 can be applied thereto in an essentially continuous pattern 32. The essentially continuous pattern 32 will have a generally higher density than the discrete regions 36 which it circumscribes. In this embodiment, the discrete regions 36 are therefore generally free of the osmotic absorbent 24.

The osmotic absorbent 24 may be applied in any desired pattern by printing. A particularly preferred method of printing is illustrated in commonly assigned U.S. patent application Ser. No. 08/154,667, entitled Process of Making Absorbent Structures and Absorbent Structures Produced Thereby, filed Nov. 17, 1993, in the names of Trokhan and Phan.

To determine whether or not an absorbent structure 20 has osmotic absorbent 24 which is freestanding, a sample of the absorbent structure 20 may be embedded in resin and microtomed, as is well known in the art. The microtomed sample is examined in elevation 28 to determine whether or not a portion of the osmotic absorbent 24 extends above the plane defined by the face of the capillary substrate 22 for the embodiments described above with respect to FIGS. 1 and 3–4 and beyond an edge of the capillary substrate 22 subtending an aperture for the embodiment of FIGS. 5–6. Of course, it is to be recognized that non-load bearing fibers of the capillary substrate 22 may extend beyond a face or edge of the capillary substrate 22, but such non-load bearing fibers are not considered, beyond their proximal ends 25 or beyond the Z-direction elevation 28 or the X-Y position where such fibers protrude beyond a face or edge of the capillary substrate 22, respectively.

EXAMPLES

Examples I and II attempt to recreate absorbent structures 20 according to the prior art. Particularly, Examples I and II duplicate the examples set forth in U.S. Pat. No. 4,061,846 issued Dec. 6, 1977 to Gross et al. Examples III and IV create absorbent structures 20 according to the present invention.

Example I

Ten grams of a 90/10 ethyl acrylate—acrylic acid latex solution containing 15 percent solids were provided. Also provided were 0.375 grams of 50% sodium hydroxide. The latex mixture and sodium hydroxide were combined at 75 degrees C. for 25 minutes to yield an approximately 15% solution of polymer. Approximately five grams of water (50% of the solution) were then evaporated to yield a 30% polymer solution. Five grams of the 30% polymer solution were then mixed with 15 milligrams of glycerin diglycidyl ether, a 1% curing agent.

The resulting solution was deposited on a filter paper. The resulting absorbent structure 20 was oven cured for 15.5 hours at 70 degrees C., then for 0.5 hours at 90 degrees C.

The resulting absorbent structure 20 demonstrated complete penetration of the osmotic absorbent 24 into the capillary substrate 22. None of the osmotic absorbent 24 was freestanding. Furthermore, the absorbent structure 20 exhibited relatively poor performance as to absorbent rate and capacity. The identical osmotic absorbent 24 material, when placed on a glass disk and cured, performed much better as to rate and capacity than when applied to the capillary substrate 22 as described above.

Example II

Ten grams of a 80/20 ethyl acrylate—acrylic acid latex solution containing 15 percent solids were provided. Also provided were 0.615 grams of 50% sodium hydroxide. The latex mixture and sodium hydroxide were slowly stirred together for 25 minutes. The resulting solution was then heated at 50 degrees C. for 22 hours to complete the saponification. Approximately four grams of water (50% of the solution) were then evaporated to yield a 25% polymer solution. The viscosity of the 25% polymer was then verified on a Brookfield viscometer at 25 degrees C. to be approximately 16,000 centipoises. Five grams of the 25% polymer solution were then mixed with 2.5 milligrams of glycerin diglycidyl ether, a 0.2% curing agent.

The resulting solution was deposited on a the low density regions 36' of a Bounty towel, available from The Procter and Gamble Company of Cincinnati, Ohio. The resulting absorbent structure 20 was oven cured for 20 minutes at 150 degrees C.

The resulting solution was thickly gelled and hence impractical to print or spray onto a capillary absorbent substrate, or to otherwise apply to a capillary substrate 22. A glass stirring rod would not fall, under its own weight, to the side of a beaker containing this solution.

Example III

Acrylic acid in the amount of 525 grams (7.3 moles) and having a molecular weight of 72 was diluted with 250 grams of deionized water. Separately, 438 grams (5.5 moles) of sodium hydroxide, molecular weight 40, at fifty weight percent was diluted with 250 grams of deionized water. The sodium hydroxide and acrylic acid mixtures were blended together, neutralizing the acrylic acid. Then 1.8 grams of N,N' methylene bis acrylamide, having a molecular weight of 154, were added to the neutralized mixture. The resulting solution was sparged with nitrogen for approximately 30 minutes. After sparging, 9 grams of 2,2-dimethyl-2-phenyl-acetophenone, having a molecular weight of 256.3 were added to the sparged solution to form a superabsorbent polymer.

To this superabsorbent polymer, 15 grams of carboxymethylcellulose were added, to control the viscosity within the range of at least 2,000 centipoises. The resulting solution was suitable for printing and yielded a freestanding osmotic absorbent when printed upon a fibrous substrate, particularly filter paper, and then in situ cross-linked under an ultraviolet lamp.

Example IV

Five hundred milliliters of acrylic acid were mixed with 1,000 milliliters of deionized water. One cup of dry ice was added to this solution to keep it cool. Slowly and while stirring, 438 grams of fifty percent sodium hydroxide solution were added to the diluted acrylic acid. Additional dry ice was then added to cool the solution to approximately room temperature.

Five grams of 2,2-dimethyl-2-phenyl-acetophenone photoinitiator were then stirred into the solution. One milliliter of triallylamine having a molecular weight of 137 was added, while stirring, as a crosslinking agent. Four aliquots of 10 grams each carboxymethylcellulose were added to this solution, while stirring, in order to increase the viscosity.

The resulting solution was clear to translucent and free of particles, clumps, and gel beads. The viscosity was high enough that when the solution was printed onto a Bounty paper towel, available from The Procter and Gamble Company of Cincinnati, Ohio, the print pattern did not noticeably change in one minute.

The resulting absorbent structure was placed under an ultraviolet lamp and irradiated for approximately ten minutes to effect a cure. The polymer thus formed readily absorbed water and expanded. The print pattern remained intact after absorbing water. The absorbent structure 20 absorbed approximately fifty to one hundred times its weight of water on a grams per gram basis. After multiple trials, it was generally found the rate of absorption was dependent upon the pattern, noting that a finer pattern yielded a faster acquisition rate.

What is claimed is:

1. An absorbent structure comprising:

a generally planar fibrous capillary substrate; and at least one site of an in situ polymerized osmotic absorbent hydrogel polymer having a proximal end joined to said fibrous capillary substrate, said osmotic absorbent hydrogel polymer further having a distal end freestanding from said capillary substrate, whereby said distal end can expand without constraint from said substrate upon imbibing liquids, said fibrous capillary substrate comprising regions of two different densities, an essentially continuous network high density region and a plurality of discrete low density regions, wherein said sites of the osmotic absorbent hydrogel polymer are disposed on said low density regions.

2. An absorbent structure comprising:

a generally planar fibrous capillary substrate defining an X-Y plane and a Z-direction orthogonal thereto; and at least one site of an in situ polymerized freestanding osmotic absorbent hydrogel polymer joined to said fibrous capillary substrate and extending outwardly therefrom in the Z-direction whereby at least one said site of freestanding osmotic absorbent hydrogel polymer can expand in the X-Y plane without constraint from said substrate upon imbibing liquids, said fibrous capillary substrate comprising regions of two different densities, an essentially continuous network high density region and a plurality of discrete low density regions, wherein said sites of the osmotic absorbent hydrogel polymer are disposed on said low density regions.

3. An absorbent structure according to claim 2 wherein said osmotic absorbent hydrogel polymer is distributed on said fibrous capillary substrate and joined thereto in a plurality of discrete sites and said fibrous capillary substrate comprises an essentially continuous network in which said sites are disposed.

4. An absorbent structure according to claim 2 wherein at least one said site of the freestanding osmotic absorbent hydrogel polymer is joined to said fibrous capillary substrate at a proximal end of said site of osmotic absorbent hydrogel polymer, and has interfiber penetration of said fibrous capillary substrate at said proximal end.

5. An absorbent structure according to claim 1 wherein at least one said site of the freestanding osmotic absorbent hydrogel polymer is joined to said fibrous capillary substrate at a proximal end, and has interfiber penetration of said fibrous capillary substrate at said proximal end.

6. An absorbent structure comprising a generally planar fibrous capillary substrate and at least one site of an osmotic absorbent hydrogel polymer joined thereto, said absorbent structure made by the process comprising the steps of:

providing a generally planar fibrous capillary substrate;

providing a liquid precursor;

increasing the kinematic viscosity of said liquid precursor to at least 2,000 centipoise;

disposing said liquid precursor on said substrate in at least on discrete site; and in situ polymerizing said liquid precursor to form at least one discrete site of an osmotic absorbent hydrogel polymer joined to said substrate at a proximal end of said discrete site of said osmotic absorbent hydrogel polymer and having a distal end freestanding from said substrate, whereby said distal end can expand without constraint from said substrate upon imbibing liquids.

7. An absorbent structure made according to the process of claim 6 wherein said step of increasing said kinematic viscosity comprises the step of adding a thickening agent to said liquid precursor.

8. An absorbent structure made according to the process of claim 6 wherein said step of increasing said kinematic viscosity comprises partially prepolymerizing said liquid precursor.

* * * * *